United States Patent [19]

Scherlag

[11] Patent Number: 5,320,642
[45] Date of Patent: * Jun. 14, 1994

[54] METHOD FOR ALLEVIATING AND DIAGNOSING SYMPTOMS OF HEART BLOCK

[75] Inventor: Benjamin J. Scherlag, Oklahoma City, Okla.

[73] Assignee: Board of Regents for the University of OK, Oklahoma City, Okla.

[*] Notice: The portion of the term of this patent subsequent to Jan. 28, 2009 has been disclaimed.

[21] Appl. No.: 823,500

[22] Filed: Jan. 22, 1992

Related U.S. Application Data

[63] Continuation-in-part of Ser. No. 531,960, Jun. 1, 1990, Pat. No. 5,083,964.

[51] Int. Cl.$^5$ .............................................. A61N 1/362
[52] U.S. Cl. .......................................................... 607/9
[58] Field of Search ................................. 128/419 PG

[56] References Cited

U.S. PATENT DOCUMENTS

| | | |
|---|---|---|
| 3,253,596 | 5/1966 | Keller, Jr. ............... 128/419 PG |
| 3,939,844 | 2/1976 | Pequignot ............... 128/419 PG |
| 4,055,189 | 10/1977 | Auerbach et al. ........ 128/419 PG |
| 4,201,219 | 5/1980 | Gonzalez ................ 128/419 PG |
| 4,222,386 | 9/1980 | Smolnikov et al. ....... 128/419 PG |
| 4,305,396 | 12/1981 | Wittkampf et al. ....... 128/419 PG |
| 4,543,963 | 10/1985 | Gessman ................ 128/419 PG |
| 4,554,922 | 11/1985 | Prystowsky et al. ..... 128/419 PG |
| 4,577,634 | 3/1986 | Gessman ................ 128/419 PG |
| 4,579,119 | 4/1986 | Callaghan .............. 128/419 PG |
| 5,083,564 | 6/1990 | Scherlag ................ 128/419 PG |

Primary Examiner—William E. Kamm
Attorney, Agent, or Firm—Dunlap, Codding & Lee

[57] ABSTRACT

A method for alleviating and diagnosing syndromes of heart block wherein a stimulus is continuously or intermittently delivered via a single electrode catheter at a site in a heart in close proximity to the A-V junction in the heart. The subthreshold stimuli were sufficient to cause impulses in the atrium to pass through the damaged His bundle to the ventricle and the stimuli were set at a level below a level required to excite the heart tissue. The delivery of the stimuli alleviates the symptoms of heart block. In one application, the delivery of the stimuli is used for diagnosing heart block when delivery of the stimuli induces the symptoms of heart block in the patient with partial or covert conduction disease.

6 Claims, 3 Drawing Sheets

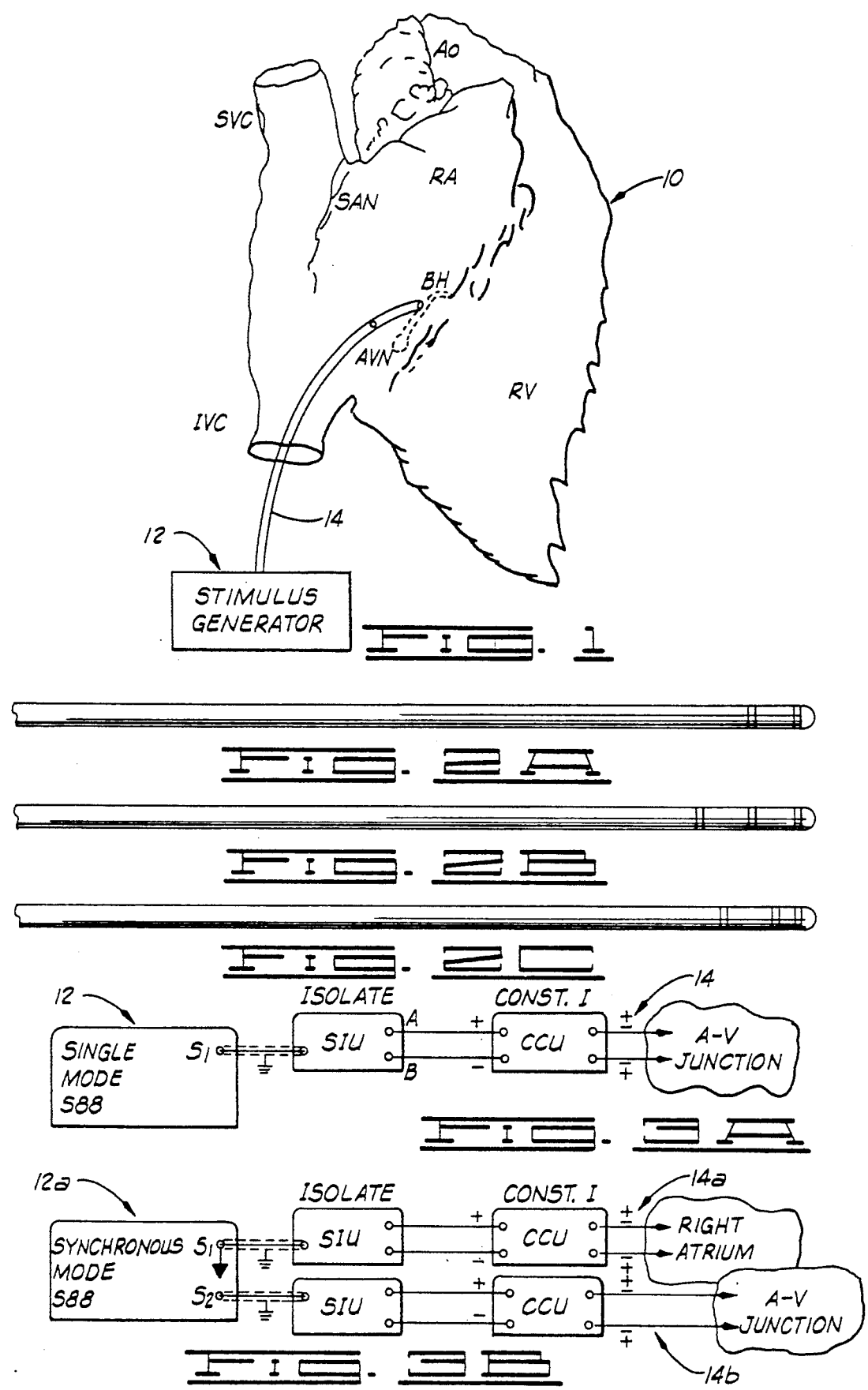

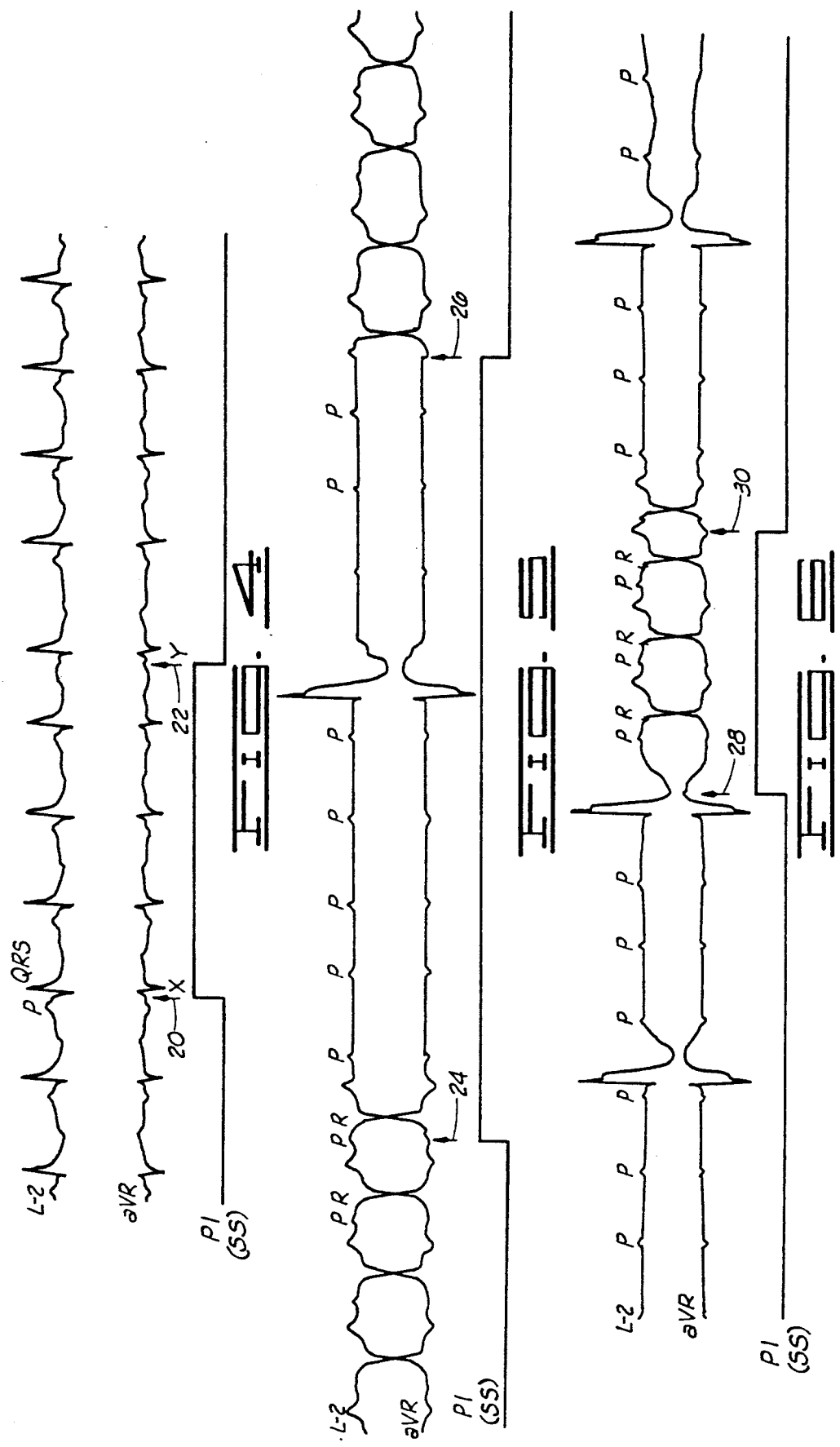

METHOD FOR ALLEVIATING AND DIAGNOSING SYMPTOMS OF HEART BLOCK

BACKGROUND OF THE INVENTION

This application is a continuation-in-part of U.S. Ser. No. 531,960, filed Jun. 1, 1990, entitled, "Method For Alleviating and Diagnosing Symptoms of Heart Block", now U.S. Pat. No. 5,083,964.

FIELD OF THE INVENTION

The present invention generally relates to a method for alleviating heart block by restoring and maintaining 1:1 conduction by delivering a subthreshold stimuli to the heart.

BRIEF DESCRIPTION OF THE DRAWINGS

FIG. 1 is a diagrammatic, schematic representation of a mammalian heart as seen through a right, lateral thoracotomy and showing the placement of an electrode catheter at the atrioventricular (A-V) junction in the region of the His bundle.

FIG. 2A, 2B and 2C are diagrammatic representations of three catheters with ring electrodes at the tip and with the ring electrodes being spaced at various distances from the tip. The electrode catheters shown in FIG. 2 constitute prior art electrode catheters which are suitable for use in the present invention for delivering subthreshold stimuli to the His bundle area.

FIG. 3A is a schematic view of a stimulus generator and other components consisting of isolation and constant current units. Also shown is a diagram of the connection of the stimulus generator to the heart. The stimulus generator and components particularly shown in FIG. 3A represent a laboratory model which was used to deliver stimuli in the form of a constant current DC pulse in the experiments described herein relating to the present invention.

FIG. 3B is a diagrammatic view of the same generator and components modified to deliver trains of stimuli to the heart. The stimulus generator particularly shown in FIG. 3B represents a laboratory model of a stimulus generator used in the experiments described herein relating to the present invention.

FIG. 4 is a diagrammatic view showing a recording of the electrical activity of a mammalian's normal functioning heart and illustrating that the delivery of the stimulus (a DC constant current signal) at the A-V junction in close proximity to the His bundle does not affect conduction through the A-V junction in the normal heart.

FIG. 5 is a recording of the electrical activity of a mammalian's heart wherein the heart has been ischemically damaged due to anterior septal artery ligation and illustrating that the delivery of the stimulus (a DC constant current signal) in accordance with the present invention induces heart block thereby indicating that this particular heart now is imminently susceptible to heart block.

FIG. 6 is a recording of the electrical activity of a mammalian's heart wherein the stimulus (a DC constant current signal) has been delivered at the A-V junction in close proximity to the His bundle in accordance with the present invention of the ischemically damaged heart after the predicted occurrence of a complete A-V heart block and illustrating that the delivery of the stimulus alleviates the symptoms of heart block by restoring 1:1 A-V conduction.

FIG. 7 illustrates that the delivery of the stimulus alleviates the heart block symptoms, in a manner similar to that described before with respect to FIG. 6, but the stimulus in this instance were more particularly a train of intermittent pulses rather than a continuous DC pulse.

FIG. 8A, is a recording of electrical activity of a dog's heart wherein the first two traces are standard electrocardiographic leads II (L-2) and aVR and the second trace is the His bundle trace.

FIG. 8B is a recording of electrical activity of a dog's heart where a subthreshold current was delivered to the right ventricular apex.

DESCRIPTION OF THE PREFERRED EMBODIMENTS

Figure 7A:
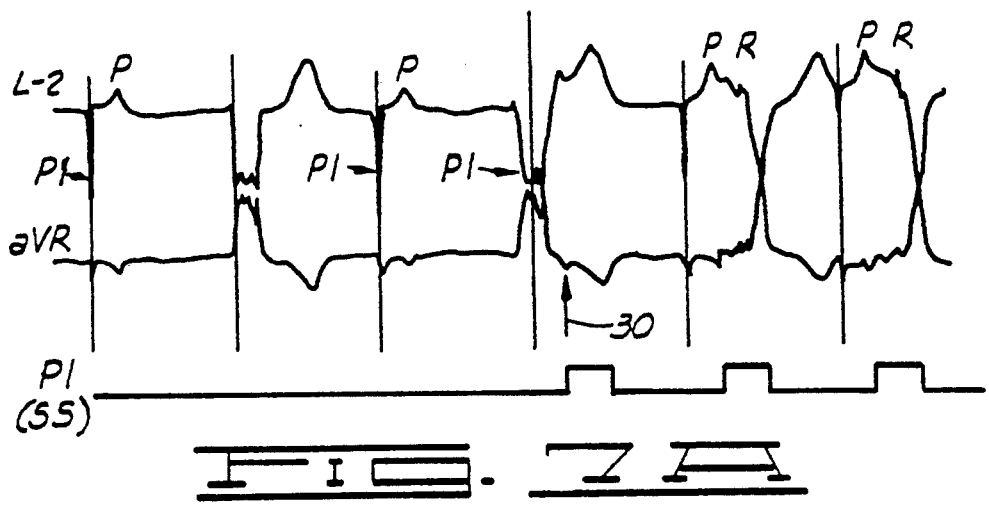
FIGS. 7A, 7B and 7C are diagrammatic views of a recording of the electrical activity of a mammalian's heart with FIG. 7B being a continuation from FIG. 7A and with FIG. 7C being a continuation of FIG. 7B.

It is well known that in the heart block syndrome, also known as Stokes-Adams attacks, heart block occurs intermittently and abruptly or paroxysmally. The method of the present invention are utilized for alleviating the symptoms of heart block in one aspect, and the method of the present invention are utilized to diagnose future or impending susceptibility of heart block in one other aspect. In accordance with the method of the present invention, a stimulus is continuously delivered via a single electrode catheter to the A-V junction in close proximity to the His bundle and the delivery of these stimuli alleviates the symptoms of heart block and restores sufficient pumping function.

The stimuli are electrical signals having amplitudes sufficient to cause impulses in the atrium of the heart to pass through the damaged His bundle to the ventricle of the heart yet the amplitude of these electrical signals are below a level required to excite the heart tissue. The electrical signal can be a constant current DC signal having a current amplitude sufficient to cause impulses in the atrium to pass through the damaged His bundle to the ventricle of the heart yet the amplitude of the constant current DC signal is below a level required to excite the heart tissue. In one other embodiment, the stimuli may be a train of current pulses with each pulse having an amplitude sufficient to cause impulses in the atrium of the heart to pass through the damaged His bundle to the ventricle of the heart and with each pulse having an amplitude below a level required to excite the heart tissue. Since the present invention particularly is adapted to be incorporated in a device implanted in a patient, the train of pulses is believed to be the preferable form of the stimuli since less energy will be required per unit time and the power pack in the implanted apparatus should have a longer life span.

In one embodiment, it has been found that susceptibility to heart block can be diagnosed by delivering the stimuli to the A-V junction in close proximity to the His bundle. When the stimuli are delivered to the heart and heart block symptoms are induced, a high susceptibility to spontaneously occurring heart block is indicated. Thus, in this embodiment, the present invention is utilized to diagnose susceptibility to future or impending heart block in patients.

Diagrammatically shown in FIG. 1 and designated therein by the general reference numeral 10 is a mammalian heart as seen through a right, lateral thoracotomy. It should be noted the experiments described herein were performed on an anesthetized dog. However, it should be emphasized that the present invention is particularly suitable for implanting in humans and the implantation procedures in humans are well known in the art. As shown in FIG. 1, the abbreviation "SVC" designates the superior vena cava; the abbreviation "IVC" designates the inferior vena cava; the abbreviation "SAN" designates the sino-atrial node; the abbreviation "AVN" designates the atrio-ventricular node (sometimes referred to herein as the A-V node); the abbreviation "AO" designates the aorta; the abbreviation "RA" designates the right atrium; the abbreviation "BH" designates the bundle of His (sometimes referred to herein as the His bundle); the abbreviation "RV" designates the right ventricle. Together the A-V node and His bundle constitute the A-V junction.

Shown in FIG. 2A is a bipolar electrode catheter with ring electrodes situated one centimeter apart. This electrode catheter is commercially available and commonly used in the art. FIG. 2B shows a tripolar electrode catheter with the ring electrodes spaced one centimeter apart and this electrode catheter also is commercially available and commonly used in the art. FIG. 2C shows a tripolar electrode catheter with a bipolar pair of electrodes at the tip situated one to two millimeters apart and a more proximal electrode ring one centimeter from the tip, and this electrode catheter is commercially available and commonly used in the art. Any of these electrode catheters is suitable for use in the present invention.

In the present state of the art there are other electrode catheters which consist of screw-in leads so that the tip of the catheter can be affixed to the cardiac muscle at various sites in the heart. Such anchored catheters can be used for chronic pacing whereas the wedged catheter placement herein is for the purpose of description in acute applications of the new pacing modality.

As shown in FIG. 1, a stimulus generator 12 is connected to the heart 10 by way of an electrode catheter 14. The electrode catheter 14, more particularly, is a bipolar electrode catheter of the type shown in FIG. 2A in this particular application. The electrode catheter is inserted through a femoral vein and the tip of the electrode catheter 14 is positioned at the A-V junction in close approximation or apposition to the His bundle. The tip of the catheter 14 is stabilized in this position in a manner well known in the art.

In general, the electrode catheter 14 is inserted into a peripheral vessel and positioned securely at the A-V junction in close proximity to the His bundle to record a specific signal from the His bundle and to deliver the stimuli to the heart. The His bundle is a structure of cardiac muscle through which all impulses from the atria (upper chambers) are conducted to the ventricles (lower chambers) of the heart and the site at which heart block has been shown to occur. The use of electrode catheters, such as the electrode catheter 14 for recording atrial and ventricle impulses and for delivering stimuli are well known in the art.

The stimulus generator 12 is constructed and adapted to generate an output of continuous or intermittent stimuli in accordance with the present invention.

One end of the electrode catheter 14 is connected to the stimulus generator 12 so that subthreshold stimuli may be outputted to the heart via the tip electrodes of catheter 14.

After securing the electrode catheter 14 to the heart (FIG. 3A), the stimulus generator 12 is adjusted to output the subthreshold stimuli. Each patient's heart is different and the stimulus generator 12 must be adjusted after the electrode catheter 14 has been implanted and secured to the heart. Initially, the stimulus generator 12 is adjusted to output a stimulus at a level sufficient to excite the heart tissue at a rate just above the spontaneous heart rate. After outputting this stimulus at a level sufficient to excite the heart tissue, the level of the output stimulus is adjusted to a level just below the level required to excite the heart tissue, this being the stimulus to be outputted by the stimulus generator 12 in accordance with the present invention. Once adjusted, the stimulus generator 12 outputs the subthreshold stimulus on a continuous basis and this stimulus is delivered to the A-V junction in close proximity to the His bundle. The delivery on a continuous basis of this subthreshold stimulus alleviates heart block and causes impulses in the atrium to pass to the ventricle via the damaged His bundle.

As mentioned before, the stimulus in one embodiment is a DC current signal and, in one other embodiment, the stimulus is a train of current pulses. When delivering a train of pulses, each pulse in the train of pulses must be delivered to the heart at a time immediately following the atrial activation (P wave). The electrode catheter 14a (FIG. 3B) delivers suprathreshold stimuli from the stimulus generator 12a at a rate just above the rate of the spontaneous heart rate. Each of these suprathreshold stimuli is outputted to the atrium and also to $S_2$ of the stimulus generator 12a. The latter is triggered to output a train of subthreshold stimuli to be delivered via catheter 14b to the A-V junction. These subthreshold stimuli are synchronously delivered just after each excited P wave and induces conduction to the ventricles through the damaged A-V junction.

As mentioned before, the present invention also can be utilized for diagnosing future susceptibility to a heart block. In this embodiment, the electrode catheter is connected to the heart in a manner exactly like that described before. The stimulus generator generates and delivers the stimuli to the A-V junction in close proximity to the His bundle in a manner exactly like that described before.

In this diagnostic application, hidden or overt partial A-V conduction damage can be exacerbated by delivery of subthreshold stimuli to the damaged His bundle. If the delivery of the subthreshold stimuli to the heart induces heart block, this indicates future high susceptibility to spontaneous occurrence of heart block. It has been found that, the delivery of subthreshold stimuli to the A-V junction, in a normal functioning heart which is not susceptible to heart block, will not affect the beating of the heart and normal atrial and ventricular sequential activation will be unaffected. On the other hand, if the delivery of the stimuli to the heart induces heart block as indicated by the received atrial and ventricular recordings, future high susceptibility to heart block is indicated and may be diagnosed.

In experiments, the electrode catheter was connected to a dog's heart at the A-V junction in close proximity to the His bundle in a manner exactly like that described before in connection with FIG. 1 and the electrode catheter was connected to a stimulus generator 12. The atrial and ventricular impulses were recorded as a standard electrocardiogram and a portion of this recording is shown in FIG. 4 with one P wave being designated by the letter "P" in FIG. 4 and one associated QRS wave being designated by the reference "R" in FIG. 4. The first wave, as shown in FIG. 4 and designated "L-2" is the electrocardiographic trace of lead II and the wave designated aVR in FIG. 4 is the mirror image lead. The traces shown in FIG. 4 reflect the normal state of the dog's heart prior to induction of damage to the A-V junction.

As indicated in FIG. 4, the dog's heart was functioning in a normal manner. A stimulus comprising a 3 milliamp DC constant current was delivered to the A-V junction in close proximity to the His bundle at a time indicated by the arrow 20 in FIG. 4, the arrow 20 indicating the time at which the continuous DC current stimuli was initiated. The switching transient caused depolarization of the His bundle producing a QRS complex, identical to the normal depolarization and the PR interval was shortened. No excitatory effect was observed during the application of this DC stimulus until the break shock indicated via the arrow 22 in FIG. 4 which again induced His bundle depolarization and a shortening of the P-R interval. With current levels between 4.5 milliamps to 7.0 milliamps regular or intermittent His bundle excitation was not produced during the period of current application; thus, these levels were subthreshold. As indicated in FIG. 4, the delivery of the stimuli did not affect the normal functioning of the dog's heart in regard to inducing heart block.

Shown in FIG. 5 is an electrocardiographic trace of lead II (L-2) and aVR in a dog wherein the anterior septal artery that supplies the His bundle was tied off to produce a damaged His bundle due to low blood flow (ischemia). As shown in FIG. 5, there was a prolongation of the A-V conduction (increased duration of the P-R interval) and appearance of an incomplete right bundle branch block pattern in the QRS complex. These changes were the result of ligation of the anterior septal coronary artery which supplies the region of the A-V junction and causes damage due to reduce blood flow to this region. A stimulus comprising a 5 milliamp DC constant current was delivered at a time indicated by the arrow 24 in FIG. 5. With the delivery of the stimulus at the time 24, heart block was induced (P waves with no associated QRS complexes. This was removed at a time indicated by the arrow 26 in FIG. 5. This indicates that the delivery of the subthreshold stimulus can induce heart block thereby indicating the future susceptibility of heart block in this particular heart and indicating the diagnostic effect of the present invention. The initial delivery of the stimulus at the time 24 induced excitation of the His bundle resulting in a ventricular complex similar in pattern to the previous spontaneous beats. Within one beat, complete A-V block ensued (only P waves, no QRS complexes) until a spontaneous ventricular escape beat occurred. Cessation of the stimulus at the time 26 permitted immediate resumption of a 1:1 A-V conduction.

Several minutes after the experiment just described and as a result of progressive ischemia (low blood flow) at the A-V junction, spontaneous complete heart block occurred in which repetitive and regular P waves were intermittently interrupted by escape ventricular beats at a very slow rate, as is indicated in FIG. 6. When the stimulus (a 5 milliamp DC constant current signal) was applied at a time 28 (FIG. 6), 1:1 A-V conduction resulted, showing the previous right bundle branch block pattern. With the cessation of the subthreshold stimulus at a time 30 (FIG. 6) a single His bundle activation occurred as the result of the break shock and was followed by resumption of complete heart block. Re-establishment of 1:1 A-V conduction was maintained as long as the subthreshold stimulus (DC current) was maintained. The longest time during which such stimulation was maintained during these experiments was one hour with continuous 1:1 conduction. Cessation of the stimulus resulted in return of heart block within 4 to 5 beats.

Figure 7B:
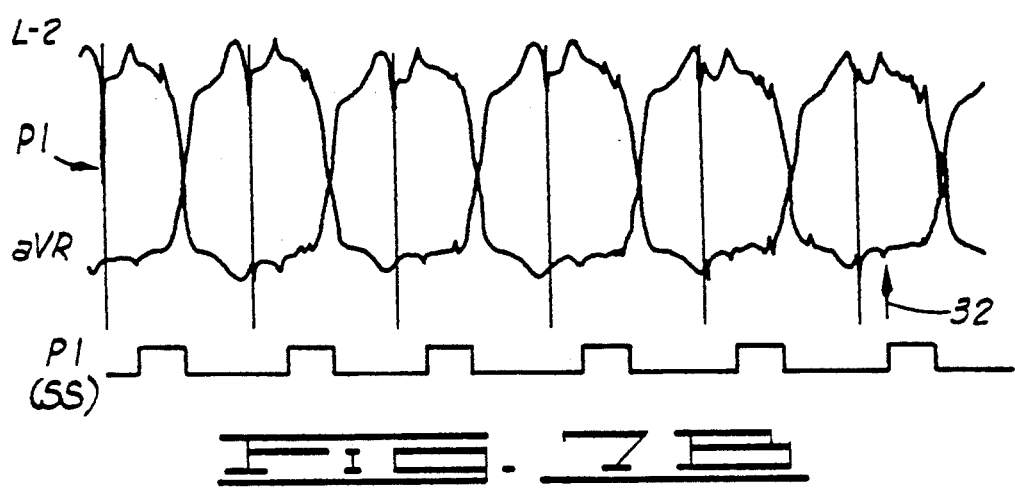
Figure 7C:

Another mode of subthreshold stimulation also resulted in reversion of A-V block to 1:1 A-V conduction. In this mode, the atria were paced (indicated in FIG. 7 by the designation "PI" which were the pacer impulses) by suprathreshold stimuli during complete heart block. These suprathreshold stimuli from S1 (in FIG. 3B) triggered the delivery of a train of subthreshold stimuli from S2 at 80–90 Hz to the A-V junction through catheter 14a (FIG. 3B). The train of subthreshold pulses were synchronized with each atrial driving stimulus and were set to occur 55 to 85 milliseconds after each driving stimulus. At a level of 4.5 milliamps applied to the damaged His bundle through catheter 14b (arrow, 30) 1:1 A-V conduction was restored and maintained with a right bundle branch block morphology shown on the ECG (FIGS. 7A and 7B). Reduction of the subthreshold train current to 4.0 milliamps (arrow 32, end of FIG. 7B) lead to 2:1 A-V conduction with right bundle branch block patterns in the conducted beats (FIG. 7C). Cessation of the stimuli was immediately followed by A-V block while suprathreshold stimuli continued to drive the atria at 180 beats per minute (same as beginning of FIG. 7A).

It is contemplated that with appropriate miniaturization, the stimulus generator 12 and the electrode catheter 14 both would be implanted in a human with an appropriate power pack to achieve the same results as the plug-in type of stimulator shown in FIG. 3 and used in the laboratory experiments described before.

The present invention provides a method for alleviating the symptoms of heart block which includes generating a subthreshold stimuli below a level required to excite the heart tissue and delivering the subthreshold stimuli to the heart. Regardless of where the heart block occurs, the subthreshold stimuli can be delivered at any position on the heart and alleviate the heart block by restoring and maintaining 1:1 conduction, as illustrated in FIG. 8A and 8B. The subthreshold stimuli can be applied at sites remote from the specific blocked zone and still achieve the same correction of heart block.

In FIG. 8A, low blood flow to the bundle of His caused by ligation of the anterior septal artery (in the dog heart) resulted in heart block. The first two traces are standard electrocardiographic leads II (L-2) and aVR. These show that for every two depolarizations of the atria (A waves) only one ventricular depolarization (V) occurs. This is known as 2:1 A-V block. Localization of the A-V block was seen in the His bundle (Hb) trace. Note that in the first beat the Hb potential, which normally shows a good amplitude and compact activation time, now shows 2 portions H, and H,, which are widely separated in time and markedly reduced in amplitude. The next beat shows failure of the cardiac impulse to cross the block so that the atria (A) and initial His bundle (H') are activated but the impulse does not depolarize the rest of the His bundle, nor the ventricles (no 2nd "V") occurred.

In FIG. 8B subthreshold current at 3.0 ma was delivered in the form of a constant DC pulse to the right ventricular apex. This site is 4–6 centimeters distant from the His bundle, i.e., the site of the A-V block. Yet, during the delivery of the constant current, upper part of FIG. 8B 1:1 A-V conduction was induced. In the lower part of the panel the current was terminated (indicated by the baseline shift, DC off) and within 4 beats 2:1 A-V block returned.

Changes may be made in the construction and the operation of the various components and assemblies described herein and changes may be made in the steps or sequence of steps of the methods described herein without departing from the spirit and the scope of the invention as defined in the following claims.

What is claimed is:

1. A method for alleviating the symptoms of heart block comprising:

generating a subthreshold stimuli below a level required to excite the heart tissue; and delivering the subthreshold stimuli to the heart for alleviating heart block, the stimuli being sufficient to cause impulses in the atrium to pass to the ventricle and the stimuli being below a level required to excite the heart tissue.

2. The method of claim 1 wherein the step of delivering the subthreshold stimuli is further defined as delivering the subthreshold stimuli.

3. The method of claim 1 wherein the step of delivering the stimuli further comprises:

connecting one end of an electrode catheter to the heart and connecting the opposite end of the electrode catheter for receiving the subthreshold stimuli; and conducting the subthreshold stimuli through the electrode catheter and delivering the stimuli to the heart via the connection of the one end of the electrode catheter to the heart.

4. The method of claim 1 wherein the stimuli is a DC current having an amplitude sufficient to cause impulses in the atrium to pass to the ventricle and the amplitude being below a level required to excite the heart tissue.

5. The method of claim 1 wherein the stimuli is a train of pulses with each pulse having an amplitude sufficient to cause impulses in the atrium to pass to the ventricle and the amplitude being below a level required to excite the heart tissue.

6. The method of claim 1 wherein the step of delivering the subthreshold stimuli as further defined as delivering the subthreshold stimuli intermittently.

* * * * *

UNITED STATES PATENT AND TRADEMARK OFFICE
CERTIFICATE OF CORRECTION

PATENT NO. : 5,320,642
DATED : June 14, 1994
INVENTOR(S) : Benjamin J. Scherlag

It is certified that error appears in the above-identified patent and that said Letters Patent is hereby corrected as shown below:

Cover Page, under "Related U.S. Application Data", [63], line 2, please delete "5,083,964", and substitute therefore --5,083,564--.

Column 1, line 10, please delete "5,083,964", and substitute therefore --5,083,564--.

Column 6, line 59, please delete "H, and H,,", and substitute therefore --H' and H''--.

Column 8, line 3, after "stimuli", please insert --continuously--.

Signed and Sealed this

Twenty-eight Day of February, 1995

Attest:

BRUCE LEHMAN

*Attesting Officer*          *Commissioner of Patents and Trademarks*

UNITED STATES PATENT AND TRADEMARK OFFICE
CERTIFICATE OF CORRECTION

PATENT NO. : 5,320,642
DATED : June 14, 1994
INVENTOR(S) : Benjamin J. Scherlag

It is certified that error appears in the above-identified patent and that said Letters Patent is hereby corrected as shown below:

In the drawing;
Please insert Figure 8A as illustrated below.

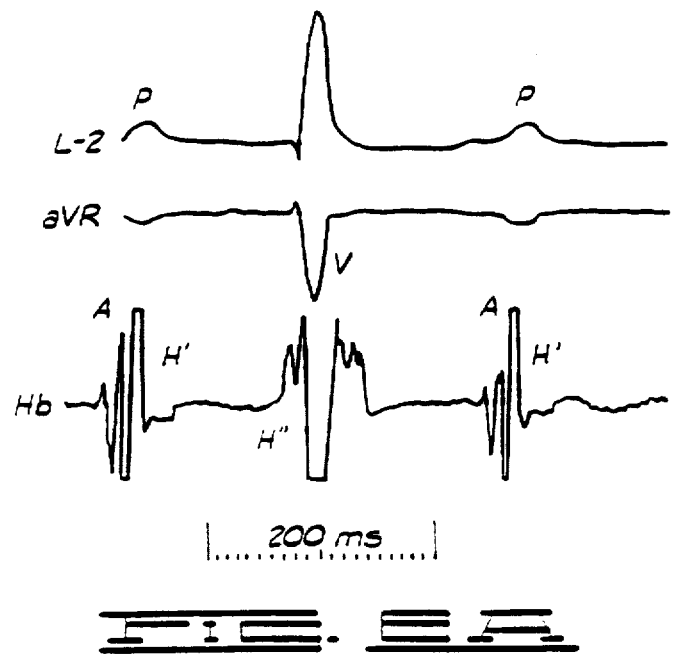

UNITED STATES PATENT AND TRADEMARK OFFICE
CERTIFICATE OF CORRECTION

PATENT NO. : 5,320,642
DATED : June 14, 1994
INVENTOR(S) : Benjamin J. Scherlag

It is certified that error appears in the above-identified patent and that said Letters Patent is hereby corrected as shown below:

Please insert Figure 8B as illustrated below.

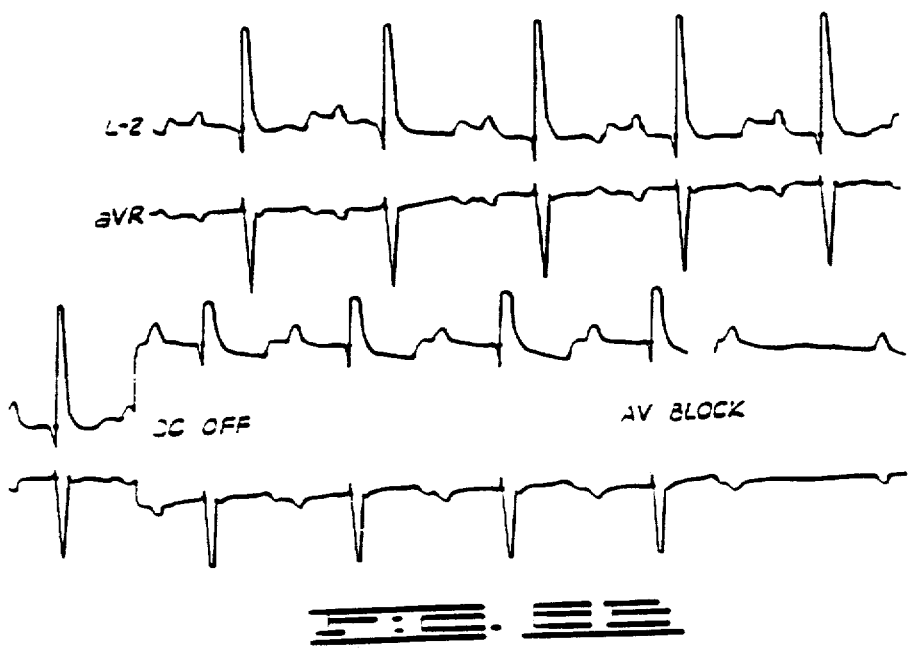

FIG. 8B